United States Patent [19]
Dykster et al.

[11] Patent Number: 5,615,244
[45] Date of Patent: Mar. 25, 1997

[54] REAL TIME RADIOGRAPHIC INSPECTION SYSTEM

[75] Inventors: Kerry R. Dykster, West Haven; Jeffrey P. England, Clinton; Philip M. Ealy, Ogden; Michael Furman, Eden; Kim R. Merritt, Brigham; Ronda R. Devereaux, Layton, all of Utah

[73] Assignee: Morton International, Inc., Chicago, Ill.

[21] Appl. No.: 450,452

[22] Filed: May 25, 1995

[51] Int. Cl.⁶ ............................................. G01N 23/04
[52] U.S. Cl. ........................................ 378/57; 378/177
[58] Field of Search ................................. 378/58, 57, 62, 378/208, 209, 195, 177, 178, 179, 180

[56] References Cited

U.S. PATENT DOCUMENTS 5,097,494  3/1992  Pantelleria et al. .................. 378/57

OTHER PUBLICATIONS

Phillips, Automated X-Ray Inspection System Group Operations Manual Jan. 27, 1993.
LumenX Automatic Inspection System Manual (No publication date or author provided).
Synergistic Detector Designs, Automatic Real-Time Radiographic InspectionSystem Operations Manual, May 1991.

*Primary Examiner*—Don Wong
*Attorney, Agent, or Firm*—Roger J. French; Gerald K. White

[57] ABSTRACT

A real time radiographic test system comprises a protective housing and a conveyor for conveying articles to be tested through the housing. A real time radiographic test instrument is located in the housing for performing a real time radiographic test on the article. The real time radiographic test instrument includes X-ray equipment disposed for directing an X-ray beam within the housing in a direction which does not intersect the conveyor. An article-handling actuator is located in the housing for repositioning an article from the conveyor to a position in registry with the X-ray beam, for maintaining the article in registry with the X-ray beam while the real time radiographic test is performed on the article and thereafter returning the article to the conveyor. The article-handling actuator and the X-ray equipment are designed such that each article to be tested is positioned substantially identically relative to the X-ray beam.

19 Claims, 7 Drawing Sheets

REAL TIME RADIOGRAPHIC INSPECTION SYSTEM

BACKGROUND OF THE INVENTION

The present invention is directed to a real time radiographic inspection system for testing articles such as production parts or assemblies. While the invention will be disclosed herein with specific reference to the use of such an inspection system for inspecting an airbag inflator for an automotive vehicle airbag, it should be appreciated that the invention may also be utilized for the inspection of other articles, such as production parts or assemblies.

It is often desirable in the production process of various parts and assemblies to provide for an online testing or inspection of the part, assembly or subassembly at various stages prior to further processing. Elimination of unacceptable parts or assemblies at appropriate points in the production process is often highly desirable in automated high volume, high speed production operations. In order to maintain the efficiency of the process, it is desirable that such inspection or testing take place in the actual production line without requiring removal and replacement of parts in the line and without appreciably slowing the production process. Thus, cycling of parts for testing or inspection and the entire test or inspection cycle should preferably be maintained in the production line without interfering with the production equipment itself, its placement in the line or the operational speed of the production process or line.

In the case of real time radiographic (RTR) inspection, a number of benefits, but also a number of shortcomings, have been experienced with prior art equipment and methods. For example, real time radiographic testing involves the X-ray imaging in real time of the articles, such as parts or assemblies, to be inspected. Criteria can be established for judging the acceptability or unacceptability of the images produced by such a system, such that unacceptable articles can be removed from the production process at an appropriate point. The use of appropriate data processing equipment in connection with such imaging can further store data corresponding to such images and the records of tested articles for later verification, for recall purposes, or the like.

The use of X-ray imaging equipment requires the provision of an appropriate shielded enclosure or housing for the imaging equipment. This requirement in turn leads to a requirement for automated handling of the articles which are to be tested inside of the housing to accomplish the individual X-ray imaging of the articles without physical entry of an operator into the housing. These requirements have lead to a number of problems with the prior art real time radiographic equipment.

For example, it is desirable that the article handling equipment within the X-ray enclosure consistently handle and position each article relative to the X-ray beam to assure consistent imaging results for all tested articles. It is also desirable that this article handling system be relatively simple, rugged and reliable and relatively easy to realign or repair. Similarly, it is desirable to maintain the proper geometry of the X-ray components to assure the consistent production of an acceptable and consistent image for each article. In this regard, it is also desirable to provide for relatively fast and simple adjustment of the alignment of the X-ray components and preferably, the X-ray equipment should be capable of real time, "X-ray on", image alignment.

As a further matter, the X-ray image should preferably also be visually inspectable to verify the acceptability or unacceptability of the article, such as a part or assembly, being tested. As a related matter, it is desirable that the X-ray components be relatively reliable and have low down time, being relatively easy to access for repair as necessary, so as to minimize interference with the production process.

As a still further matter, it is also desirable that the real time radiographic inspection system and components, including its enclosure, be relatively easy to assemble, and be capable of performing on-line testing (without removing the articles from the line) on existing production lines or conveyors and related machinery and equipment, without requiring extensive redesign and reconstruction of the existing production line. It is also desirable that the equipment take up as little floor space as possible, because floor space is generally at a premium in high volume, high speed production facilities. As a related matter, it is desirable that the real-time radiographic (RTR) systems, including its enclosure, be relatively simple and easy to digassemble and reassemble to service another location or accommodate modifications to the production process and equipment.

Generally speaking, the prior art real time radiographic (RTR) systems for inspecting inflators have not always provided all of the foregoing desirable features. For example, with respect to the article handling and positioning systems, prior art real time radiographic test instruments utilized a que system. This que system would mechanically present a predetermined amount of product to the real time radiographic test instrument. In order to que product, the prior art system would remove the product from the normal process line and introduce it into a separate, machine X-ray enclosure. This que system required a number of sophisticated mechanical systems, such as sets of tooling to position the articles, an index table, a complex three-part gripping system and a complex product entrance and exit system with respect to the X-ray enclosure.

The use of such complicated parts and systems multiplies the number of areas in which malfunction can occur resulting in disturbance of the production process, or in misalignment or inconsistent handling of articles, resulting in inconsistent test results. The requirement that the articles be removed from the production process to accomplish the test can also interfere with the production process, by using a relatively cumbersome system for removal and reintroduction of parts or articles with respect to the production process.

The prior art RTR inflator inspection systems have provided relatively cumbersome and complex internal article handling components and arrangements in which it has been difficult to maintain consistent alignment for consistent imaging by the X-ray beam. Real time, "X-ray on" image alignment was not possible. Some of these prior art systems have utilized relatively complex servo-motor alignment components, which never quite achieve the same positioning of an article relative to the X-ray beam from one article to another. Moreover, both the handling and X-ray imaging parts of the prior art systems had generally been designed such that they are relatively difficult to access, and difficult to adjust, realign or repair, requiring excessive down time in the production cycle to accomplish such adjustment, realignment or repair.

With respect to the enclosures or housings of prior art machines, these were generally designed around the articles and the relatively complex handling systems discussed above. This in turn usually created a relatively large, heavy cabinet that would be difficult to relocate and would limit machine reconfiguration, making all but the most simple changes very difficult or even impossible. Generally such cabinets were assembled by welding or similar means, such that they could not readily be disassembled for relocation, for example, to be redeployed at different points in the production process, or reconfiguration, for example, to accommodate redesign of the production equipment. As an additional matter, these prior art enclosures or housings were also generally quite large, owing to the large amount of space necessary for the extensive and complex article handling equipment to be housed therein, thereby taking up large amounts of factory floor space.

With respect to reject systems of the prior art, similar considerations apply as those discussed above with respect to article handling in general. Prior art systems generally used relatively complex article handling arrangements for removing failed articles following the completion of real time radiographic testing. These relatively complex handling systems also required relatively large amounts of floor space, were relatively expensive and inefficient and difficult to debug or troubleshoot, requiring extensive system down time to effect repairs.

OBJECTS AND SUMMARY OF THE INVENTION

Accordingly, it is a general object of the present invention to provide a real time radiographic inspection system which provides the above-discussed desirable features and overcomes the above-discussed shortcomings of the prior art.

Briefly, and in accordance with the foregoing objects, the present invention provides a real time radiographic test instrument comprising a protective housing; conveyor means for conveying an article to be tested through said housing; real time radiographic testing means located in said housing for performing a real time radiographic test on said article; said real time radiographic testing means including X-ray means disposed for directing an X-ray beam within said housing and in a direction not intersecting said conveyor means; actuator means located in said housing for repositioning an article from said conveyor means to a position in registry with said X-ray beam, for maintaining said article in registry with said X-ray beam while said real time radiographic test is performed on said article, and for thereafter returning said article to said conveyor means, said actuator means being located and configured for positioning each article to be tested substantially identically relative to said X-ray beam.

In accordance with another aspect of the invention, there is provided a method for performing a real time radiographic test on a production part, comprising the steps of verifying the presence of an acceptable identifying code on an article; producing a good data indication in the presence of an acceptable identifying code and a bad data indication in the absence of an acceptable identifying code; holding an article until a real time radiographic test instrument is ready to test the article; performing a real time radiographic test on an article and producing corresponding test data; causing an article to bypass said real time radiographic test without being tested in response to said bad data indication; analyzing said test data and producing said good data indication if said test data is acceptable and a said bad data indication if said test data is not acceptable; removing a corresponding article in response to said bad data indication.

In accordance with yet a further aspect of the invention, there is provided a real time radiographic inspection system for carrying out the foregoing method.

BRIEF DESCRIPTION OF THE DRAWINGS

The features of the present invention which are believed to be novel are set forth with particularity in the appended claims. The organization and manner of operation of the invention, together with further objects and advantages thereof may best be understood by reference to the following description, taken in connection with the accompanying drawings in which like reference numerals identify like elements, and in which:

DETAILED DESCRIPTION OF THE ILLUSTRATED EMBODIMENT

Figures 1, 2, 3, 4:
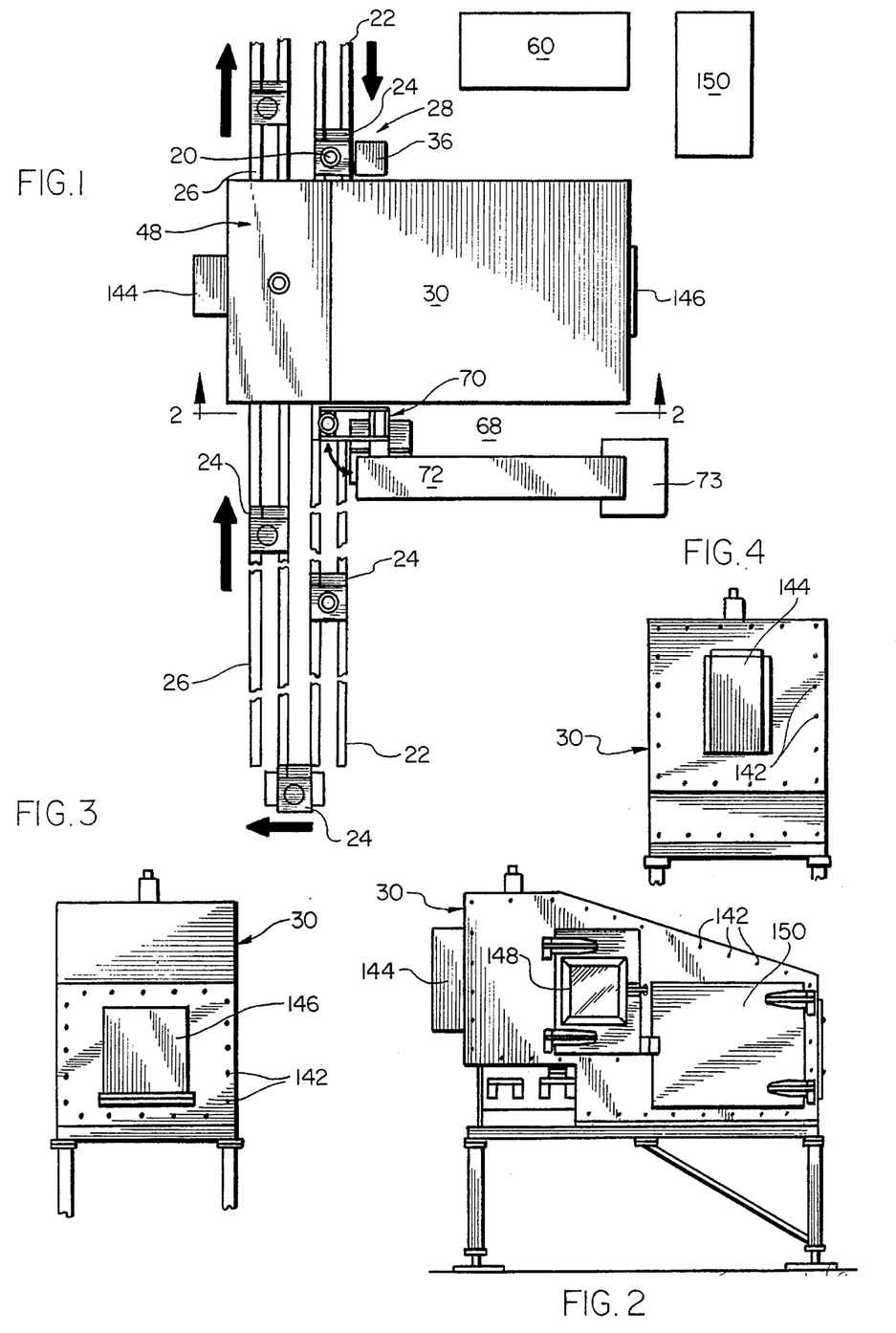
FIG. 1 is a top plan view of a real time radiographic inspection system in accordance with the present invention.
FIG. 2 is an elevation of the system taken generally along the line 2—2 of FIG. 1.
FIG. 3 is an end view of the enclosure of the system of FIG. 1.
FIG. 4 is an end view of the enclosure opposite the end shown in FIG. 3.

Referring now to the drawings and initially to FIG. 1, a real time radiographic inspection system in accordance with the invention is illustrated. The invention is described herein with specific reference to a real time radiographic (RTR) system for testing automotive airbag inflator units or assemblies, which will hereinafter be referred to as "articles". In the illustrated embodiment these articles 20 are carried by a first conveyor or belt 22 which preferably is a part of the production line in connection with which the real time radiographic system is to be utilized. In the illustrated embodiment, the articles 20 are carried on pallets 24 which in turn rest on and are carried by the conveyor 22. The conveyor 22 carries the articles 20 to be tested, on pallets 24, through a real time radiographic (RTR) test instrument which is located within a protective enclosure or housing 30. The articles are palletized or placed on pallets 24 for purposes of being carried through the real time radiographic test instrument. Accordingly, a second or return conveyor 26 is utilized for returning pallets 24 after use in conveying an article 20 through the real time radiographic system, to a starting point for receiving subsequent articles to be tested.

At a reject station 68, a reject assembly 70 removes articles 20 rejected by the test procedure from the conveyor 22. Good articles 20 are transferred to another conveyor (not shown), which delivers the articles 20 to the next step in the assembly process. Empty pallets are transferred from conveyor 22 to return conveyor 26.

Figure 5:
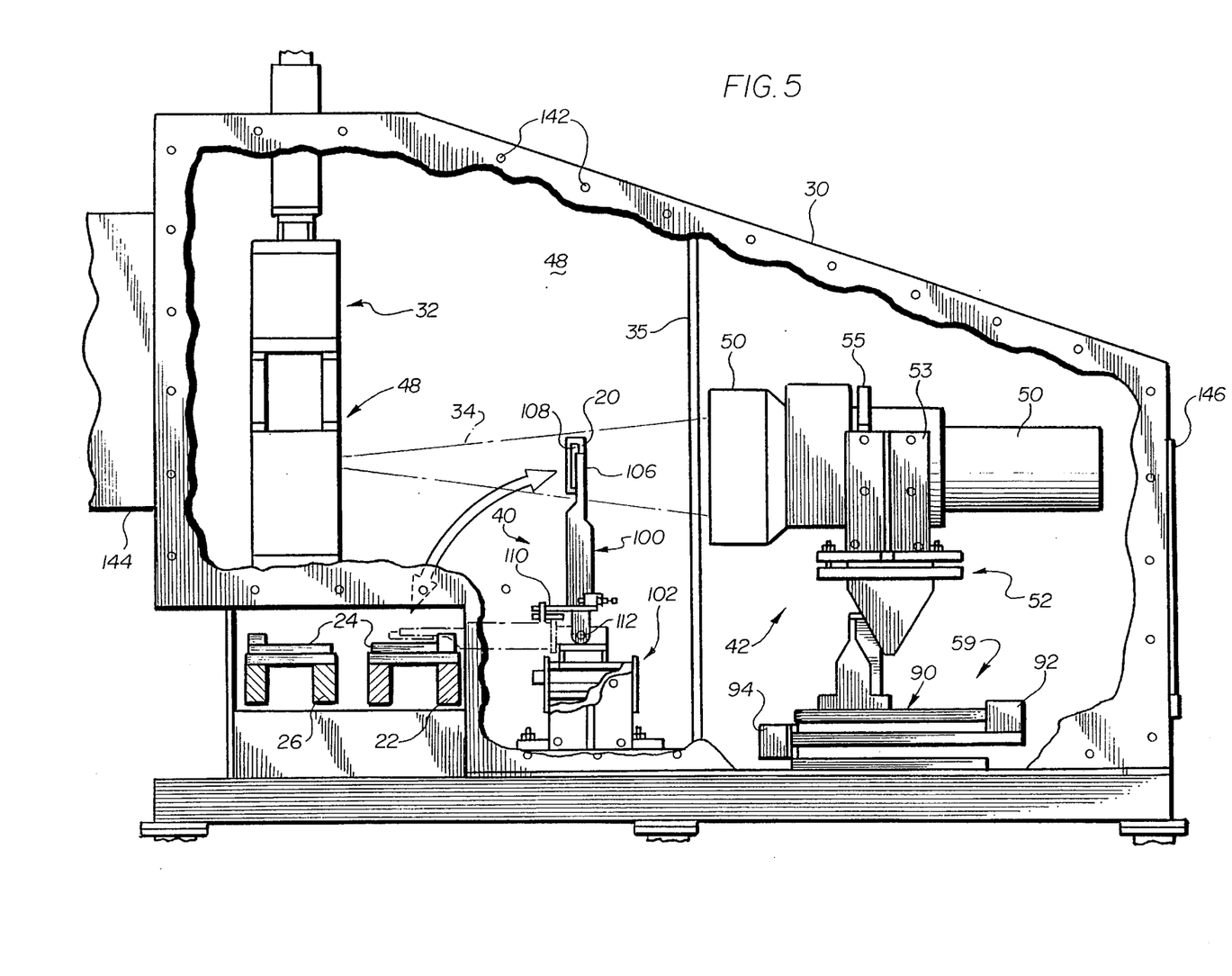
FIG. 5 is an enlarged elevation similar to FIG. 2 and partially broken away, showing additional internal details.
Figure 6:
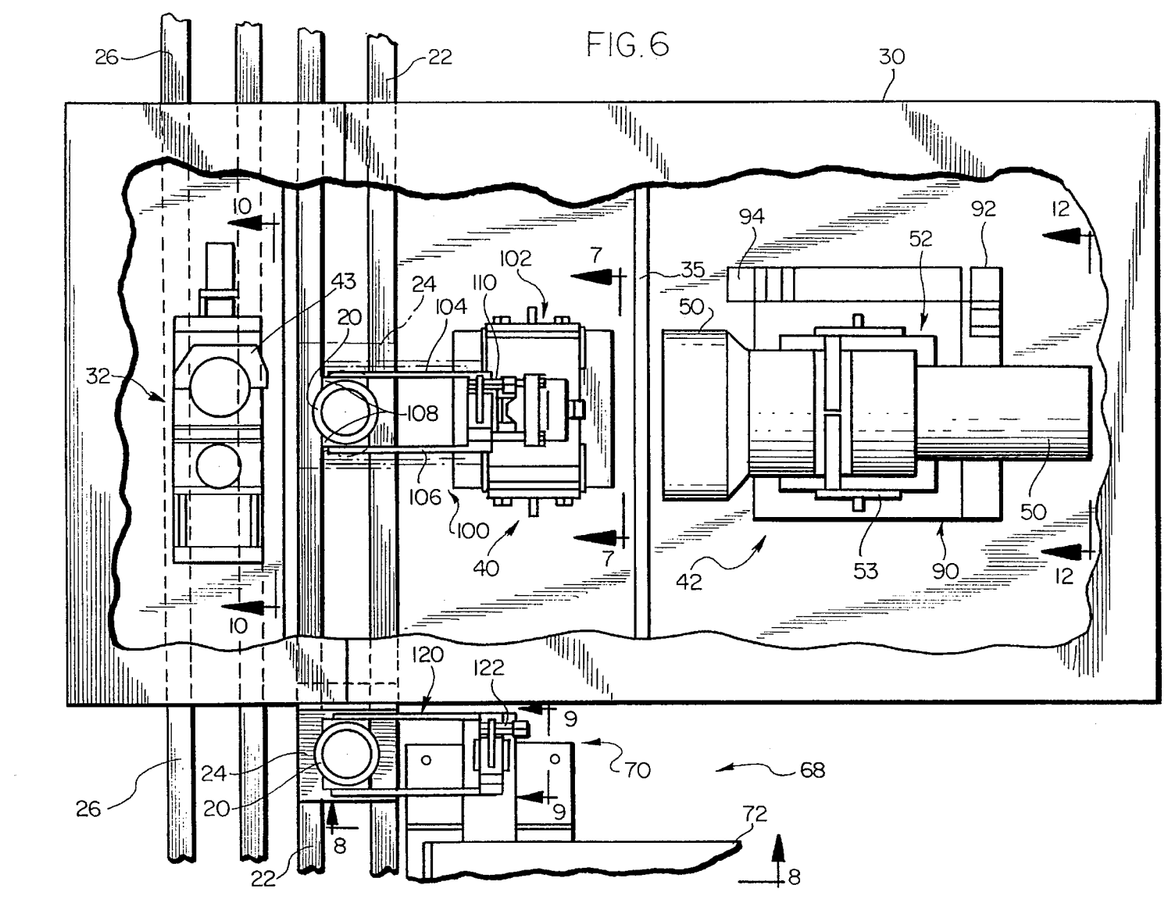
FIG. 6 is an enlarged top plan view, partially broken away, and showing additional internal details.

As best viewed in FIGS. 5 and 6, the RTR test instrument includes an X-ray source 32 disposed for directing an X-ray beam 34 transversely across the conveyor 22 and spaced there-above, within the housing 30. In order to hold an article 20 in-the path of the X-ray beam 34 for testing, an actuator assembly 40 is provided in the housing 30 for engaging an article 20 on a pallet 24 on the belt or conveyor 22 and repositioning this article to a position in registry with the X-ray beam 34 from the source 32. This actuator assembly 40 is further configured for maintaining the article 20 in registry with the X-ray beam 34 while a real time radiographic test is performed on the article and for thereafter returning the article 20 to its associated pallet 24 on the conveyor 22. Advantageously, this actuator assembly 40, as will be more fully described hereinafter, is located and configured for positioning each article 20 substantially identically relative to the X-ray beam 34 to assure consistency in the test data obtained.

Figures 10, 11, 12:
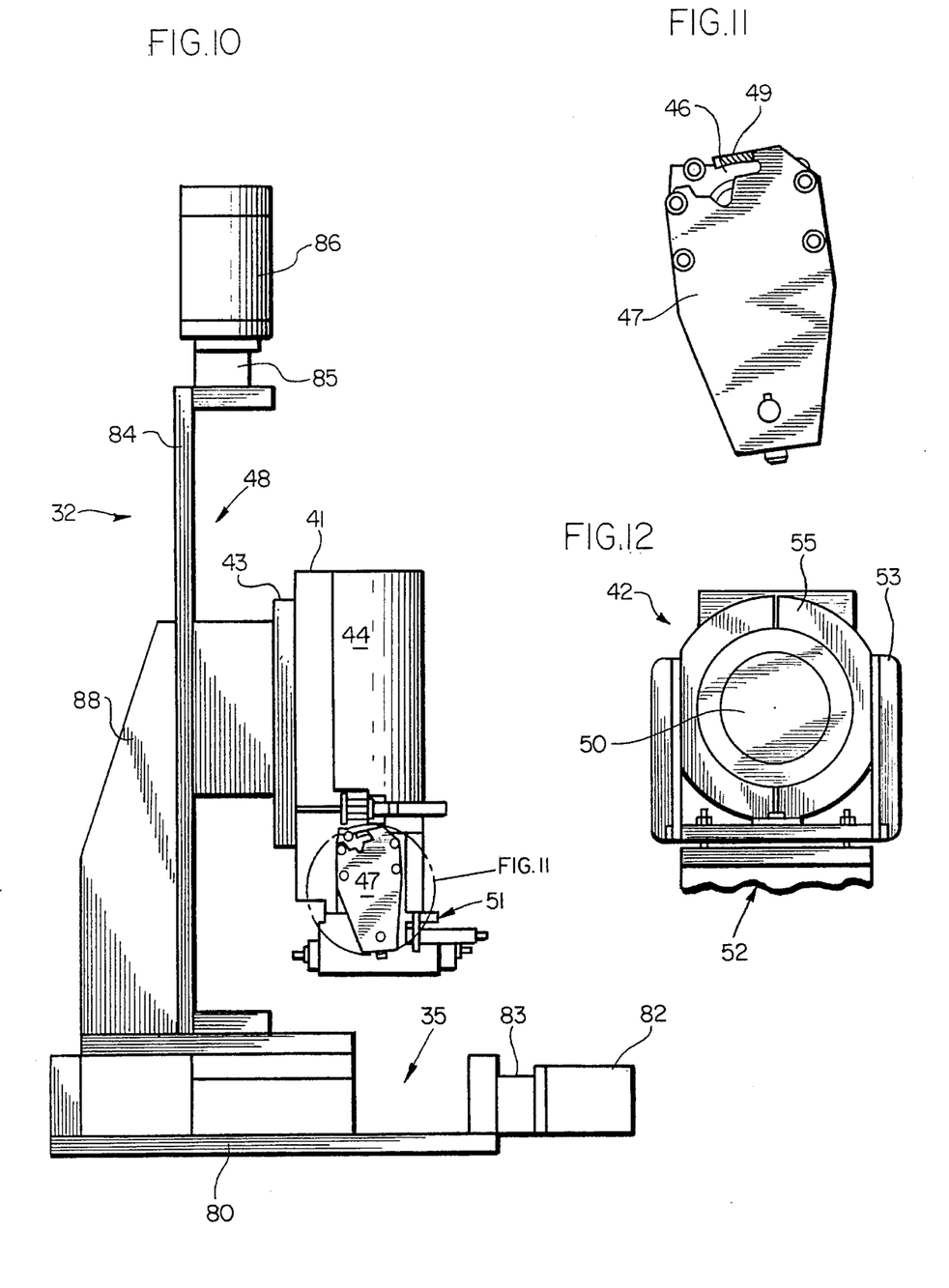
FIG. 11 is an enlarged elevation of a component of FIG. 10.
FIG. 12 is an end elevation of a portion of an image intensifier assembly, taken generally along the line 12—12 of FIG. 6.
Figure 13:
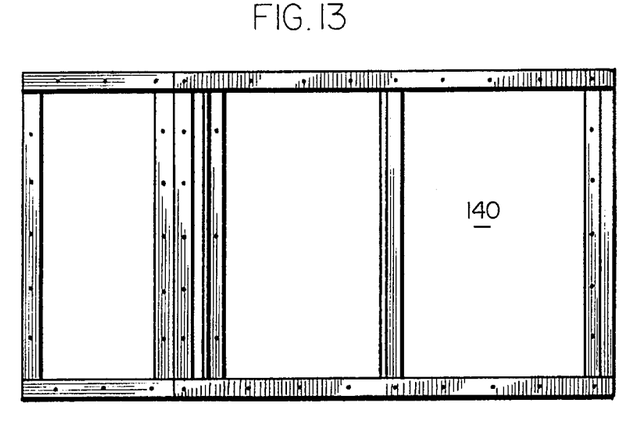
FIG. 13 is a top plan view of a frame for the cabinet of FIGS. 1 and 4.
Figure 14:
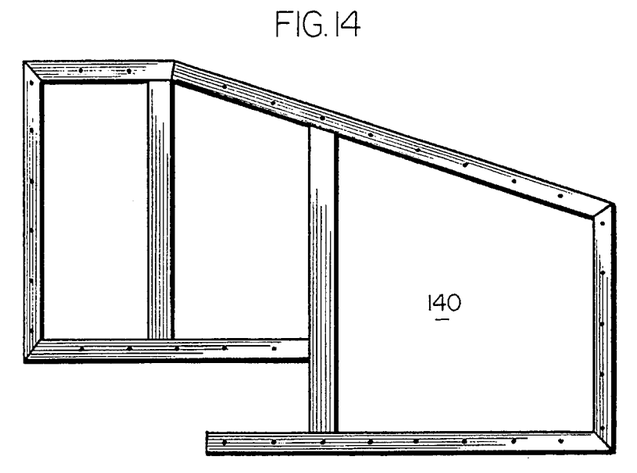
FIG. 14 is an elevation of the frame of FIG. 8.
Figure 15:
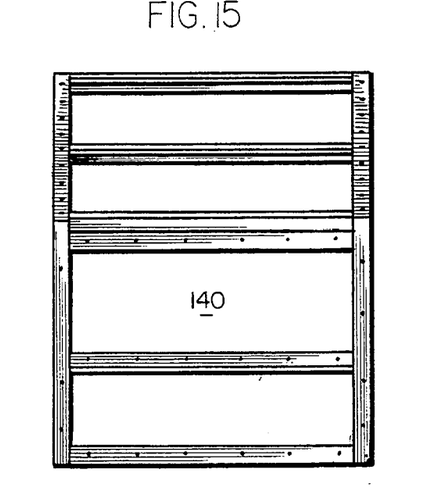
FIG. 15 is an end view of the frame of FIG. 8.

The X-ray equipment within the housing includes both the X-ray source 32 and an image intensifier assembly 42. The X-ray source 32 includes an X-ray tube 44 and a collimator 46 (see FIG. 11) operatively coupled with the X-ray tube 44 for focusing the X-ray beam 34. A source support assembly designated generally 48 supports the X-ray tube 44 and collimator 46 in a position for focusing the X-ray beam 34 in the direction indicated. Referring also to FIGS. 10 and 11, the X-ray tube 44 is mounted to a mounting base 41 and held by a clamp 43. The mounting base 41 is carried by a mounting plate 45. The collimator 46 is mounted on a beam blocker plate 47 which also carries a beam blocker clip 49. These elements are in turn mounted to a beam blocker support 51.

The image intensifier assembly 42 includes an image intensifier 50 and an intensifier support assembly 52 for supporting the image intensifier 50 in a position generally parallel to and spaced apart from the X-ray tube 44 and in registry with the X-ray beam 34. The support assembly 52 includes a support bracket 53 and a compression ring 55 for supporting the image intensifier 50. A bulkhead 35 divides the enclosure 30, just in front of the image intensifier 50. This bulkhead is constructed of steel and lead (preferably lead on the side facing the X-ray tube 44), and has a central, generally circular through opening to permit the focused X-ray beam 34 to reach the image intensifier 50, while confining remaining X-ray energy to the other side of the enclosure 30.

Preferably, the face of the image intensifier is provided with a lead mask (not shown) having a central circular opening sized to reduce the area upon which the X-ray beam impinges to a diameter which will correspond to a predetermined magnification factor of the diameter of the article 20. In one example, the article 20 is an inflator of 4.09 in. diameter, the diameter of the opening in the bulkhead is about 6 in;, and the diameter of the opening in the mask is 5.27 in. The use of the mask minimizes X-ray scatter. The use of the collimator 46 and mask on the image intensifier gives an inspectable image having a full spectrum of contrast of from 0 to 255. That is, a processor 60 breaks down the image to 255 different gray levels, with 0=black and 255=white.

Accordingly, the processor or data processing means 60, which is indicated diagrammatically in FIG. 1, cooperates with the X-ray equipment thus far described to perform an automated X-ray inspection of the articles 20 on a full image using a 360° regions of interest format. The data processing means 60 is responsive to data corresponding to the X-ray image received from the image intensifier 50 for producing a good data indication in response to an acceptable X-ray image of a tested article and a bad data indication in response to an unacceptable image of a tested article.

A reject means or assembly 70 is located adjacent the conveyor 22 where it exits the X-ray enclosure or housing 30. This reject assembly 70 is responsive to a bad data indication from the data processing means 60 for removing the corresponding article 20 from the conveyor 22. In this regard, the reject assembly may include a reject chute or conveyor 72 for receiving a rejected article 20 from the reject assembly 70 and delivering it to a suitable reject holding area or a non-conformance box or "lock box" 73 as it is sometimes referred to.

Without limiting the invention in any way, but for purposes of giving a specific example, the X-ray source tube 44 may be a Comet Model MXR160 X-ray source tube. The image intensifier 50 may be a 9-inch dual field straight image intensifier, LumenX Model No. 0362-0011, available for example from AFP Imaging Corporation, Richmond, Va.

In accordance with a feature of the invention, the X-ray source and image intensifier assemblies 32 and 42 include means for adjusting the position of the X-ray beam 34 so as to achieve real time, X-ray on, image alignment. That is, it is possible to respectively adjust the source and the image intensifier relative to an article 20 for achieving a desired alignment of the X-ray image obtained, under the control of the processor 60, which includes control means for controlling the operation of the article handling and image producing parts of the RTR system.

As best viewed in FIG. 10, the X-ray source assembly 32 includes X-ray tube positioning means 35 for adjusting the position of the X-ray beam 34 in two orthogonal directions. In the illustrated embodiment, the positioning means 35 comprises an X table 80 and a drive motor 82 for positioning the X-ray tube 44 in the X direction, and a Z table 84 and motor 86 for adjusting the position of the X-ray tube 44 in the Z direction. In the illustrated embodiment, the X and Z tables preferably comprise Design Concepts parts #67336-20-2 and #6738-20-2, respectively. The motors preferably comprise Design Concepts parts #2373-00 (motor 82) and #1349-53 (motor 86), the latter being designated as "motor with brake". The respective motors 82 and 86 are further preferably provided with suitable couplings 83, 85, preferably Design Concepts part #8032-00 with respect to motor 82 and #1918-02 with respect to motor 86. The Z table 84 is preferably supported by an upright support bracket 88, Design Concepts part #4536-55 and motor 86 is preferably provided with a Design Concepts #1624-00 frame adaptor. All of the foregoing Design Concepts parts may be obtained from Design Concepts, Inc., Franklin, Mass.

The image intensifier assembly 32 includes positioning means 59 coupled with the support assembly 52 for selectively adjusting the position of the image intensifier 50 in three orthogonal directions. In the illustrated embodiment, this positioning means 59 includes a three-axis coordinate table 90, an X/Y axis motor 92 and a Z axis motor 94 for driving the coordinate table 90 in each of the three orthogonal directions to achieve corresponding positioning of the image intensifier 50. In the illustrated embodiment the three-axis coordinate table 90 is preferably Design Concepts part #4536-52 and the X/Y axis motor is an MC-002 motor, Design Concepts part #2373-00. A coupling (not shown) for the X/Y axis motor, Design Concepts part #8032-00, is also provided. The Z axis motor is an MC-033 motor, Design Concepts part #4503-50 and a coupling (not shown) for the Z axis motor, Design Concepts part #1918-09, is provided. The foregoing Design Concepts parts are also available from Design Concepts Inc., Franklin, Mass.

In accordance with the invention, the respective motors for positioning the X-ray source or tube 44 and image intensifier 50 are remotely controlled from the data processor 60.

Figure 7:
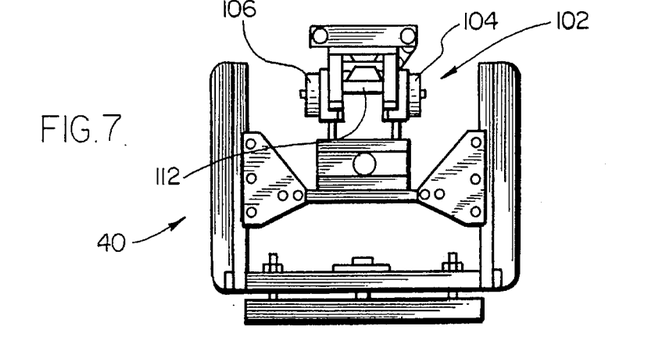
FIGS. 7, 8, 9 and 10 are views taken generally along the lines 7—7, 8—8, 9—9 and 10—10 of FIG. 6, respectively.

The actuator means or assembly 40, as best viewed in FIGS. 5, 6 and 7, includes a gripping means or assembly 100 for selectively engaging and releasing an article 20 and a pivoting means or assembly 102 for pivotally moving the gripping means 100 between a position in registry with an article 20 carried by the conveyor 24 and a position for holding the article 20 engaged by the gripping means 100 in registry with the X-ray beam 34. In the illustrated embodiment, the gripping means 100 include a pair of elongated gripping arms 104, 106 which are provided with gripping pads 108 at their terminal ends. These gripping pads 108 are of complementary shape for engaging and holding the articles 20, which in the illustrated embodiment comprise relatively short generally cylindrical or disc-like inflator assemblies for automotive airbags. Thus, in the illustrated embodiment, these gripping pads 108 present generally arcuate surfaces to the inflators 20.

The gripping arms 104, 106 are moveable between a first or open position as shown in phantom line in FIG. 5, for releasing an article 20, and a closed position as shown in full line in FIG. 5, for engaging an article 20. The gripping assembly 100 includes suitable drive means for respectively opening and closing the gripping arms 104, 106, and preferably comprises a "parallel gripper" of the type generally designated as a Robohand #RPW-375-1, available from Robohand of Trumbull, Conn. A suitable sensor such as a proximity switch 110 cooperates with the processor 60 to monitor the position of the gripping arms 104, 106.

The pivoting assembly 102 pivotally moves the gripping means or assembly 100 about a pivot point 112 between a first position indicated in phantom line in FIG. 6 for engagement with or release of an article 20 on conveyor 22, respectively, and a second position shown in full line in FIG. 6 for placing the article in registry with the X-ray beam 34. A second proximity switch (not shown) is operatively coupled with processor 60 for monitoring the position of the pivoting means or assembly. The processor 60 controls the operation of the gripping means 100 and pivoting means 102 to operate in sequence and at a sufficient speed to accomplish a real time radiographic testing of an article within a 12 second cycle time, and preferably, within a 10 second cycle time. Thus, the actuator means 40 is responsive to the control means of the processor 60 for accomplishing this sequence of operation: pivot gripping arms down (in open position), close gripping arms to engage article, pivot gripping arms up and hold article in X-ray beam; pivot gripping arms down, open gripping arms.

Figure 8:
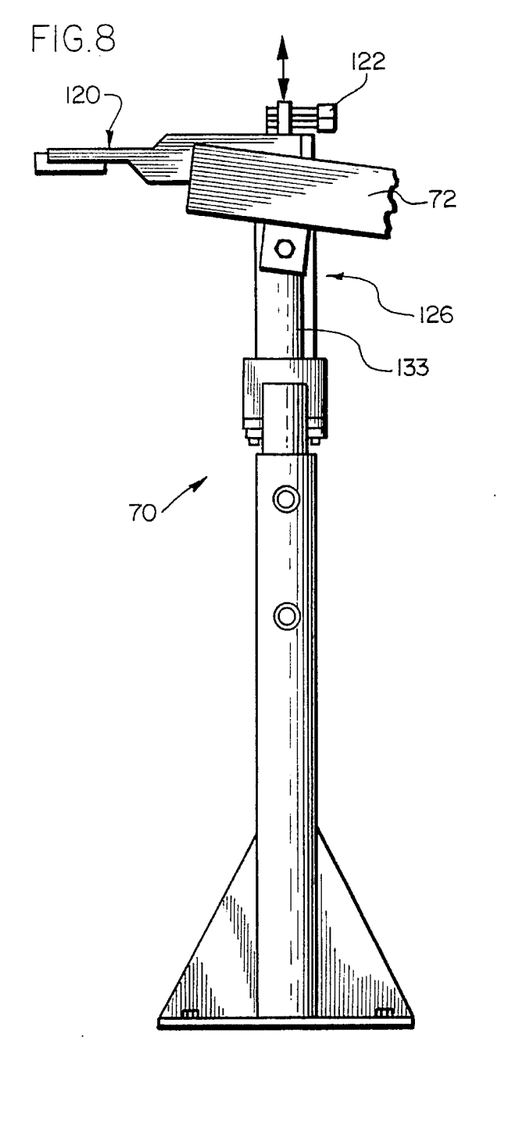
Figure 9:
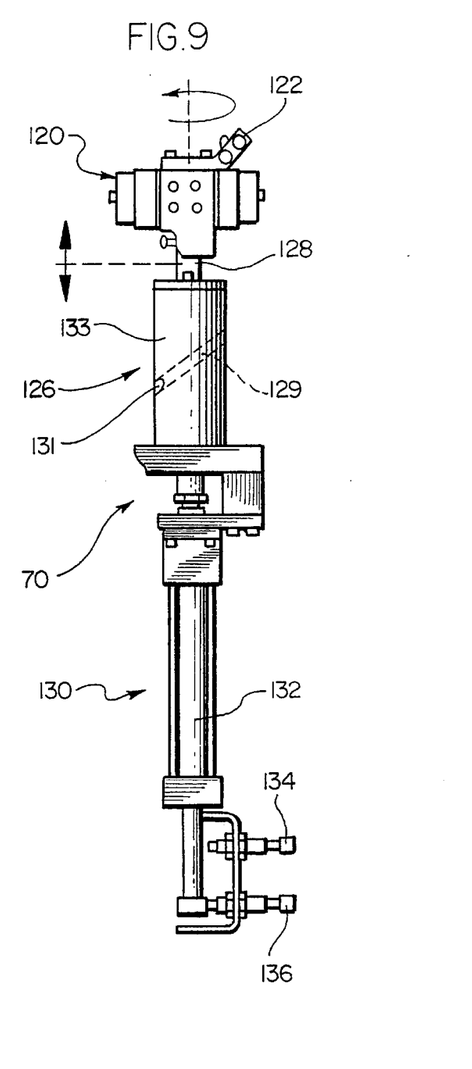

The reject means or assembly 70, as best viewed in FIGS. 6, 8 and 9, includes a gripping means or assembly 120 which is substantially identical to the gripping means assembly 100 described above, and preferably also a Robohand RPW-375-1 parallel gripper. This gripping assembly 120 is provided with a similar sensor or proximity switch 122 for cooperating with the processor 60 to monitor the position of the gripping assembly 120, either in an open position for releasing an article 20 or in a closed position for engaging an article 20. Pivoting means 126 include a pivot shaft 128 for pivotally rotating the gripping assembly 120 between a position in registry with the conveyor 22 and a position in registry with the reject chute 72.

The reject assembly 70 also includes a lifting and lowering means or assembly 130, which preferably includes a double acting cylinder 132 for raising the gripping means 120 to lift an article engaged thereby free of the conveyor 22 and up to the level of the reject chute 72. At the same time the gripping means are rotated or pivoted for depositing the article in the reject chute 72. This rotation is accomplished by the use of a generally S-curved track 129 and a follower 131 on the pivot shaft 128, such that the pivot shaft will rotate the gripping assembly 900 while moving between fully raised and fully lowered positions. The track 129 and follower 131 are inside of a housing 133 and are illustrated only diagrammatically in FIG. 9, wherein only a part of the track 129 is shown. In the illustrated embodiment, the double acting cylinder 132 is of the type generally designated 1.5 CKJTC-2AU14AC2.125 available from Parker Hannifin Corp., Rotary Actuator Division, Wadsworth, Ohio. Additional proximity sensors 134, 136 may also be provided for cooperating with the processor 60 to monitor the position of the double acting cylinder 132.

Referring now to FIGS. 1–4 and 13–15, the enclosure 30 and its frame 140 are respectively illustrated. In accordance with the invention, the frame 140 mounts a plurality of panels which together form the X-ray protective enclosure 30. These panels are removably coupled to the frame, preferably by bolts 142. This removable coupling of panels to the frame is such that the enclosure can be relatively easily dismantled, moved and reassembled or reconfigured. That is, the enclosure can be dismantled and reassembled to house radiographic inspection equipment at a different portion of an assembly line, if desired. Also, the enclosure can be readily reconfigured by changing or modifying the panels to accommodate differences in the equipment to be housed therein or in the manner in which conveyors or other members deliver parts to be inspected thereto, as well as other requirements for entry into the cabinet to inspect, adjust or repair the radiographic equipment and article handling equipment housed therein. In the illustrated embodiment a number of removable panels or doors 144, 146, 148, 150 are also illustrated for this latter purpose. These removal panels and doors preferably overlap the panels which form the walls of the enclosure.

The panels, including the removable panels and doors, are constructed of X-ray shielding material. In the illustrated embodiment the frame is preferably constructed of aluminum and the panels are constructed of lead and steel. Preferably, each panel is at least two layers, with the inside layer being lead and the outside being steel (i.e., inside/outside relative to the enclosure 30). Preferably, the panels are so constructed and coupled with the frame that the enclosure is capable of shielding 160kV, 4.0mA of X-ray energy.

Referring again to FIG. 1, a code reading station 28 is located along the conveyor 22 just before it enters the enclosure 30. At this code reading station, a code reading apparatus such as a bar code reader 36, is provided for reading an identifying code, such as a bar code, affixed to the respective articles 20 and for producing a good data indication in the presence of an acceptable identifying code and a bad data indication in the absence of an acceptable identifying code. Similarly, a number of other stations are identified in FIG. 1, including the code reading station 28 and a pre-test station 38 at which parts art momentarily held prior to introduction into the enclosure 30 until the radiographic test instrument is ready to receive each part for testing. The radiographic test instrument is located in the enclosure 30 generally at a test station 48. Finally, the reject means or assembly 70 is located at a reject station 68 where the conveyor 24 emerges from the enclosure 30.

FIG. 1 also illustrates imaging means in the form of a video display 150. The video display 150 displays the X-ray image of an article being subjected to a real time radiographic test by the system of the invention. This displayed image is visually inspectable for verifying the findings of the automated real time radiographic test. In certain defined situations, an operator may supplement the data produced by the real time radiographic test instrument when a visual inspection of the image on the video display 150 indicates that the article is acceptable in one or more areas in which the test data has indicated unacceptability. In such an instance, the operator may make appropriate entries to the processor 60 to add data indicating that the article is acceptable and explaining why, in accordance with predefined procedures for doing so. For example, the operator may visually confirm that certain parts are present in an inflator assembly, and add to the data from the processor to reflect this, in the case where the data based upon the automated X-ray inspection has indicated that one or more of these parts are not present.

Having thus described the components of the system of the invention, operation of the system for carrying out a real time radiographic test in accordance with the method of the invention will be described with reference to the flow chart of FIG. 16.

The processor 60 provides control means for automatically controlling the operation of the system in a predetermined sequence and a memory means responsive to both the identifying data generated by the code reader 36 and the test data generated by the radiographic test instrument or X-ray components for creating a record uniquely identifying each part tested and the corresponding test data. This record can be called upon for quality assurance, and for lot tracking and traceability at a future time. Preferably, the processor 60 also includes diagnostic means for verifying accurate operation of the real time radiographic test instrument and communicates with and controls the radiographic test instrument, including the X-ray and X-ray positioning components, the article handling components including the actuator and reject assemblies 40 and 70, and the video display 150.

Figure 16:
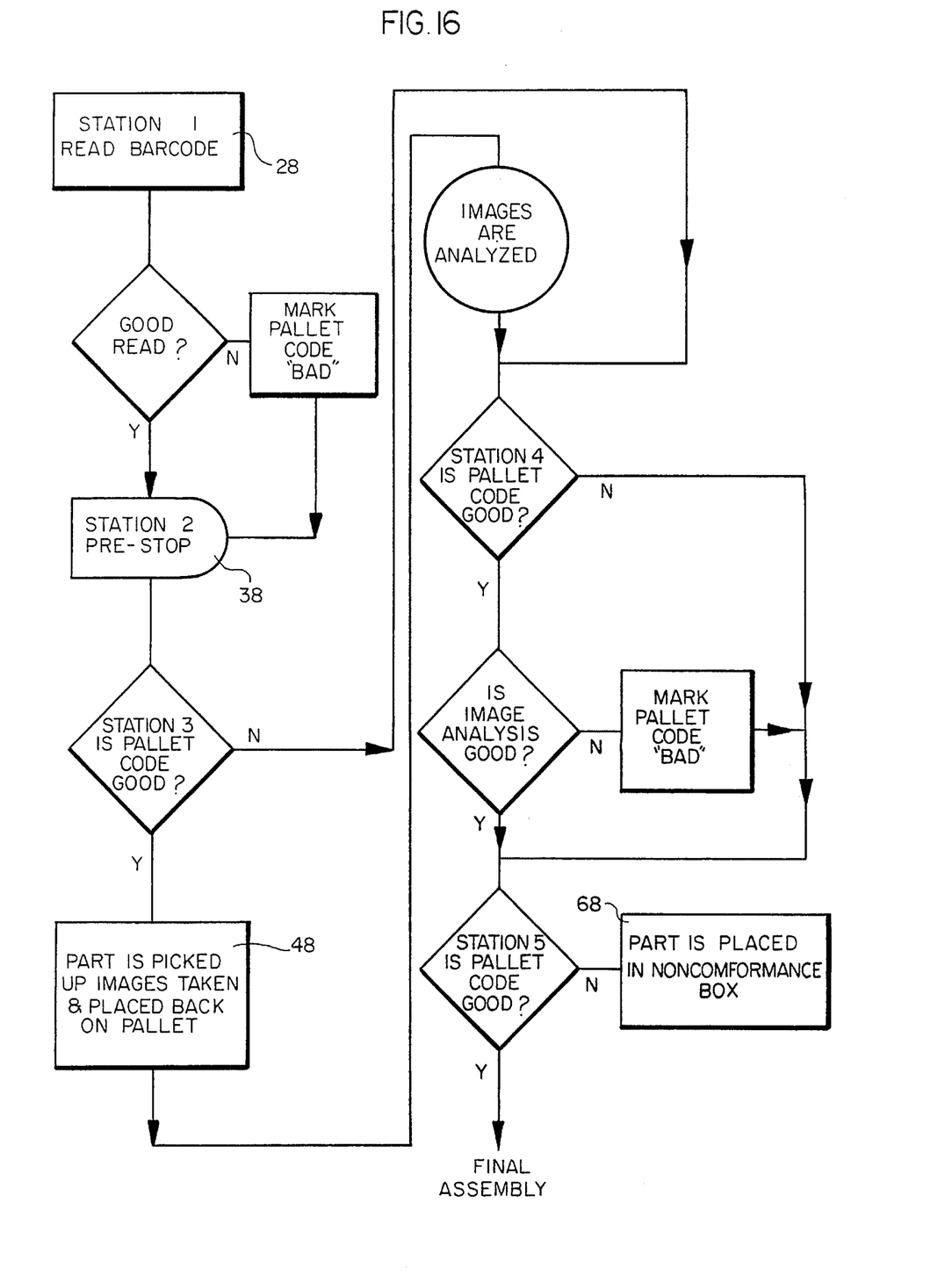
FIG. 16 is a flow chart illustrating operation of the real time radiographic inspection system of the invention.

In operation, initially an article 20 carried by a pallet 24 on conveyor 22 passes the code reading station 28 at which the bar code reader 36 attempts to read a bar code on the part (referred to as "pallet code" in FIG. 16). In cooperation with the processor 60, a good data indication will be produced in the presence of an acceptable identifying code and a bad data indication will be produced in the absence of an acceptable identifying code. At the pre-test ("PRE-STOP") station 38, a pallet 24 containing an article 20 to be tested is held until the test instrument is ready to test the article.

At the test station 48, located within the enclosure 30, the article-handling actuator assembly 40 and the X-ray components 32, 42 of the real time radiographic test instrument, cooperate under control of the processor 60 to perform a real time radiographic test upon the article 20 and produce corresponding test data. However, the processor 60 includes means for causing the corresponding article to bypass the X-ray equipment and the real time radiographic test, that is, without being tested, in the event that a bad data indication was given in the initial code reading step. The processor 60 includes means for analyzing the test data produced during the real time radiographic test and producing a good data indication if the test data is acceptable and a bad data indication if the test data is not acceptable. Finally, at the reject station 68, the reject assembly 70 is responsive to a bad data indication given either by the code reading step previously or by the real time radiographic test for removing the corresponding article from the conveyor 22.

While particular embodiments of the invention have been shown and described in detail, it will be obvious to those skilled in the art that changes and modifications of the present invention, in its various aspects, may be made without departing from the invention in its broader aspect, some of which changes and modifications being matters of routine engineering or design, and others being apparent only after study. As such, the scope of the invention should not be limited by the particular embodiments and specific constructions described herein but should be defined by the appended claims and equivalents thereof. Accordingly, the aim in the appended claims is to cover all such changes and modifications as fall within the true spirit end scope of the invention.

The invention is claimed as follows:

1. A real time radiographic test system for performing a real time radiographic test on an article, comprising: an X-ray shielding, protective housing; conveyor means for conveying an article to be tested through said housing; real time radiographic testing means located in said housing for performing a real time radiographic test on said part; said real time radiographic testing means including X-ray means disposed for directing an X-ray beam within said housing transversely across said conveyor means and spaced thereabove; actuator means located in said housing for repositioning an article from said conveyor means to a position in registry with said X-ray beam, for maintaining said article in registry with said X-ray beam while said real time radiographic test is performed on said article, and for thereafter returning said article to said conveyor means; said actuator means being located and configured for positioning each article to be tested substantially identically relative to said X-ray beam.

2. A real time radiographic test system according to claim 1 and further including processing means for cooperating with said X-ray means to perform an automated X-ray inspection of said article on a full image using a 360° regions of interest format.

3. A real time radiographic test system according to claim 1 wherein said X-ray means comprises an X-ray tube, a collimator coupled with said X-ray tube for focusing the X-ray beam, and a source support assembly for supporting said X-ray tube and said collimator in a position for focusing said X-ray beam in said first direction.

4. A real time radiographic test system according to claim 3 wherein said X-ray means further includes an image intensifier and an intensifier support assembly for supporting said image intensifier generally parallel to and spaced from said X-ray tube in a position in registry with said X-ray beam.

5. A real time radiographic test system according to claim 3 and further including X-ray tube positioning means coupled with said source support assembly for selectively adjusting the position of said X-ray beam.

6. A real time radiographic test system according to claim 4 and further including intensifier positioning means coupled with said intensifier support assembly for selectively adjusting the position of said image intensifier.

7. A real time radiographic test system according to claim 5 wherein said positioning means include remotely controlled means for adjusting the position of said X-ray beam to achieve real time, X-ray on, image alignment.

8. A real time radiographic test system according to claim 6 wherein said positioning means include remotely controlled means for adjusting the position of said image intensifier to achieve real time, X-ray on, image alignment.

9. A real time radiographic test system according to claim 1 wherein said actuator means includes gripping means for selectively engaging and releasing an article and pivoting means for pivotally moving said gripping means between a position in registry with an article carried by said conveyor means for engaging said article and a position for holding an article engaged thereby in registry with said X-ray beam.

10. A real time radiographic test system according to claim 9 wherein said actuator means is responsive to control means for operating said gripping means and said pivoting means in sequence and at a sufficient speed to accomplish real time radiographic testing of articles within a twelve second cycle time.

11. A real time radiographic test system according to claim 9 wherein said actuator means is responsive to control means for operating said gripping means and said pivoting means in sequence and at a sufficient speed to accomplish real time radiographic testing of articles within a ten second cycle time.

12. A real time radiographic test system according to claim 1 and further including X-ray image processing means responsive to said real time radiographic test for producing a good data indication in response to an acceptable X-ray image of a tested article and a bad data indication in response to an unacceptable X-ray image of a tested article, and reject means responsive to said bad data indication for removing a corresponding article from said conveyor.

13. A real time radiographic test system according to claim 12 wherein said reject means comprises gripping means for selectively engaging and releasing an article and pivoting means for pivoting said gripping means between a first position in registry with said conveyor means and a second position in registry with a reject area.

14. A real time radiographic test system according to claim 13 wherein said reject means further includes lift means for selectively lowering said gripping means to engage an article on said conveyor and for raising said gripping means to lift an article engaged by said gripping means free of said conveyor.

15. A real time radiographic test system according to claim 1 wherein said housing comprises a frame and a plurality of panels removably coupled to said frame, said panels being constructed of X-ray shielding material, and said removable coupling of said panels to said frame being such that said housing can be relatively easily dismantled, moved and reassembled.

16. A real time radiographic test system according to claim 15 wherein said frame is constructed of aluminum and said panels are constructed of lead and steel.

17. A real time radiographic test system according to claim 15 wherein said panels are coupled with said frame and are constructed of a material selected in such a manner that said enclosure is capable of shielding 160 kV, 4.0 mA of X-ray energy.

18. A real time radiographic test system according to claim 5 wherein said X-ray tube positioning means includes means for selectively adjusting the position of said X-ray beam in two orthogonal directions.

19. A real time radiographic test system according to claim 6 wherein said intensifier positioning means includes means for selectively adjusting the position of said image intensifier in three orthogonal directions.

* * * * *

UNITED STATES PATENT AND TRADEMARK OFFICE
CERTIFICATE OF CORRECTION

PATENT NO. : 5,615,244
DATED : March 25, 1997
INVENTOR(S) : Dykster et al.

It is certified that error appears in the above-indentified patent and that said Letters Patent is hereby corrected as shown below:

```
Title Page, [75], Inventors: delete "; Ronda R. Devereaux".
Col. 2, Ln. 18, correct "digassemble" to read
     -- disassemble --.
Col. 5, Ln. 21, correct "housing" to read -- housing 30 -- .
Col. 8, Ln. 13, correct "900" to read -- 90° -- .
```

Signed and Sealed this

Tenth Day of February, 1998

Attest:

BRUCE LEHMAN

*Attesting Officer*   Commissioner of Patents and Trademarks